(12) United States Patent
Kolomeitsev et al.

(10) Patent No.: US 6,184,425 B1
(45) Date of Patent: Feb. 6, 2001

(54) PROCESS FOR PREPARING FLUORINE-CONTAINING COMPOUNDS

(75) Inventors: Alexander Kolomeitsev, Kiew (UA); Sergej Pasenok, Kelkheim (DE)

(73) Assignee: Aventis Research & Technologies GmbH & Co., Frankfurt (DE)

( * ) Notice: Under 35 U.S.C. 154(b), the term of this patent shall be extended for 0 days.

(21) Appl. No.: 09/230,961

(22) PCT Filed: Aug. 6, 1997

(86) PCT No.: PCT/EP97/04284

§ 371 Date: Jul. 7, 1999

§ 102(e) Date: Jul. 7, 1999

(87) PCT Pub. No.: WO98/05610

PCT Pub. Date: Feb. 12, 1998

(30) Foreign Application Priority Data

Aug. 7, 1996 (DE) .............................................. 196 31 854

(51) Int. Cl.$^7$ .................................................... C07B 17/20
(52) U.S. Cl. .......................... 570/170; 570/124; 570/127; 544/217; 544/218; 544/224; 544/334; 544/409; 546/345; 546/346
(58) Field of Search .................................... 570/170, 124, 570/127; 544/217, 218, 334, 224, 409; 546/345, 346

(56) References Cited

U.S. PATENT DOCUMENTS 4,287,374 * 9/1981 North ................................... 568/937

FOREIGN PATENT DOCUMENTS

602598 * 6/1994 (EP) .

* cited by examiner

Primary Examiner—Johann Richter
Assistant Examiner—J. Parsa
(74) Attorney, Agent, or Firm—Frommer Lawrence & Haug

(57) ABSTRACT

The present invention relates to a process for preparing fluorine-containing compounds by reacting a compound which contains fluorine-exchangeable halogen with a fluoride or a mixture of fluorides with the formula I $$MeF \qquad (I),$$

in which Me is an alkaline earth metal ion, $NH_4^+$-ion or alkali metal ion, in the presence of a compound or a mixture of compounds of the formula (II)

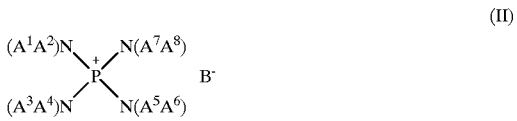

(II)

in which $A^1, A^2, A^3, A^4, A^5, A^6, A^7, A^8$ independently of one another are identical or different and are a straight-chain or branched alkyl or alkenyl having 1 to 12 carbon atoms, cycloalkyl having 4 to 8 carbon atoms, an aryl having 6 to 12 carbon atoms, or an aralkyl having 7 to 12 carbon atoms, or $A^1 A^2$, $A^3 A^4$, $A^5 A^6$, and $A^7 A^8$ independently of one another are identical or different and are connected to one another directly or by way of O or N—$A^9$ to form a ring having 3 to 7 ring members, $A^9$ is an alkyl having 1 to 4 carbon atoms and $B^-$ is a monovalent acid radical or the equivalent of a polyvalent acid radical, in the presence or absence of a solvent at a temperature from 40 to 260° C.

27 Claims, No Drawings

PROCESS FOR PREPARING FLUORINE-CONTAINING COMPOUNDS

This application is a 371 of PCT/EP97/04248 filed on Feb. 6, 1997.

The present invention relates to a process which is an improvement over the prior art for preparing fluorine-containing compounds by means of a halogen-fluorine exchange reaction.

Fluorine-containing compounds are employed, inter alia, in liquid-crystalline mixtures (EP 0 602 596).

The halogen-fluorine exchange reaction is also known by the name halex reaction. It is an extensively employed method of introducing fluorine substituents into a compound containing fluorine-exchangeable halogen.

In the case of aromatic compounds, especially activated aromatic compounds, the halogen-fluorine exchange proceeds in the manner of a nucleophilic substitution. The implementation of this reaction requires relatively high reaction temperatures, which are often between 200 and 300° C., leading to the formation of in some cases considerable amounts of decomposition products. In general it is impossible to operate without a solvent, so that the space-time yields are much lower than those of solvent-free processes. As an alternative to this it is possible to use conventional phase transfer catalysts, by means of which some of the abovementioned disadvantages can be reduced.

Other problems, such as poor stirrability of the reaction suspension in the case of solvent-free processes, continue to exist. Phase transfer catalysts used to date have been quaternary alkylammonium or alkylphosphonium salts (U.S. Pat. No. 4,287,374), pyridinium salts (WO 87/04194), crown ethers or tetraphenylphosphonium salts (J. H. Clark et al., Tetrahedron Letters 28 [1987], pages 111 to 114). Some of these phase transfer catalysts have comparatively low levels of activity and are only moderately stable at the temperatures required for the implementation of the reaction.

In view of these restrictions and disadvantages there is a great need for a process which avoids the disadvantages inherent in the known processes, especially high reaction temperatures and long reaction times, and which, moreover, provides the desired fluorine-containing compounds in yields ranging from good to very good at lower reaction temperatures and in shorter reaction times.

This object is achieved by a process for preparing fluorine-containing compounds by reacting a compound which contains fluorine-exchangeable halogen with a fluoride or a mixture of fluorides with the formula I $$MeF \quad (I),$$

in which Me is an alkaline earth metal ion, $NH_4^+$-ion or alkali metal ion, in the presence or absence of a solvent at a temperature from 40 to 260° C., which comprises carrying out the reaction in the presence of a compound or a mixture of compounds of the formula (II)

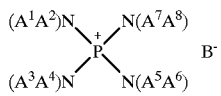

(II)

in which $A^1, A^2, A^3, A^4, A^5, A^6, A^7, A^8$ independently of one another are identical or different and are a straight-chain or branched alkyl or alkenyl having 1 to 12 carbon atoms, cycloalkyl having 4 to 8 carbon atoms, an aryl having 6 to 12 carbon atoms, or an aralkyl having 7 to 12 carbon atoms, or $A^1 A^2$, $A^3 A^4$, $A^5 A^6$, and $A^7 A^8$ independently of one another are identical or different and are connected to one another directly or by way of O or N—$A^9$ to form a ring having 3 to 7 ring members, $A^9$ is an alkyl having 1 to 4 carbon atoms and $B^-$ is a monovalent acid radical or the equivalent of a polyvalent acid radical.

It should be regarded as surprising that the use of the compounds of the formula (II) as catalyst leads to a strong acceleration of the reaction, thereby making it possible to implement the halogen-fluorine exchange reaction (halex reaction) under considerably milder conditions, in particular at lower temperatures and/or with shorter reaction times. At the same time it is also possible by this means to suppress or substantially avoid the formation of unwanted byproducts.

The novel process has other advantages as well. For instance, the compounds of the formula (II) are not toxic, or at most only slightly toxic, and in addition possess a resistance to thermal stress which is superior to that of the prior art catalysts that are frequently employed. If a compound of the formula (II) in which the radicals $A^1$ to $A^8$ are each a methyl group is used and is subjected over 10 hours to a temperature of not less than 230° C., then only 0.2% of carbonaceous decomposition products are subsequently found.

The term fluorine-exchangeable halogen refers to chlorine, bromine or iodine, especially chlorine or bromine, preferably chlorine, which can be exchanged for fluoride in the context of a nucleophilic substitution.

A further advantage of the novel process is that a large number of compounds can be employed as starting material.

Thus it is possible to employ, as the compound containing fluorine-exchangeable halogen, an aromatic compound whose ring system has from 0 to 3 nitrogen atoms and carries a chlorine or bromine substituent, in particular a chlorine substituent, which can be exchanged for fluorine which compound may have at least one further substituent which promotes nucleophilic substitution of the aromatic compound.

With no claim to completeness, suitable starting compounds for the novel process are aromatic compounds of the benzene, naphthalene, pyridine, anthracene, phenanthrene, pyrimidine and pyrazine type and of the type of benzofused ring systems of pyridine (quinoline, isoquinoline, acridine or acridone type), of pyrimidine, pyrazine and piperazine (benzodiazines of the cinnoline, phthalazine, quinazoline, quinazoline, phenazine or phenoxazine type) and derivatives thereof which may have at least one further substituent which promotes the nucleophilic substitution of the aromatic compound. This further substituent which promotes the nucleophilic substitution of the aromatic compound usually leads to an activation of the aromatic compound, which is thereby more readily amenable to a halogen-fluorine exchange reaction.

The further substituent which promotes the nucleophilic substitution of the aromatic compound comprises I and M substituents, which reduce the electron density or, respectively, the nucleophilicity of the aromatic compound and thereby make electrophilic substitution more difficult. However, the aromatic compound is thereby activated with respect to a nucleophilic substitution. The activating effect of these substituents is particularly great when they stand ortho or para to the halogen that is to be exchanged for fluorine, this halogen being, in particular, chlorine or bromine, preferably chlorine.

With no claim to completeness mention may be made, as further substituents which promote the nucleophilic substitution and thus the halogen-fluorine exchange reaction, especially the chlorine-fluorine exchange reaction, of F, Cl, Br, I, $NO_2$, NO, $CF_3$, CN, CHO, COF, COCl, $SO_2F$, $SO_2Cl$, $OCF_3$, $SCF_3$, $SOCF_3$, $SO_2CF_3$, COOR, CONRR', $SO_2R$, COR, OR or a radical —CO—O—CO—, —CO—NR—CO—, which links two ortho positions, especially F, Cl, $NO_2$, $CF_3$, CN, CHO, COCl, $SO_2Cl$, COOR, $SO_2CF_3$, CONRR', $SO_2R$, or COR, preferably F, Cl, $NO_2$, $CF_3$, CN, CHO or COCl, where R and R' each independently of one another are identical or different and are H, a straight-chain or branched alkyl having 1 to 6, especially 1 to 4 carbon atoms, an aryl having 6 to 12 carbon atoms or aralkyl having 7 to 12 carbon atoms and where the alkyls and aralkyls are unsubstituted or substituted from one to three times by halogen, especially by fluorine or chlorine.

It is possible to employ an aromatic compound which possesses on the ring system a fluorine-exchangeable chlorine or bromine substituent, especially a chlorine substituent, and which has at least one further substituent from the series consisting of F, Cl, Br, I, $NO_2$, $CF_3$, CN, CHO, COF, COCl, $SO_2F$, $SO_2Cl$, $OCF_3$, $SCF_3$, $SOCF_3$, $SO_2CF_3$, COOR, CONRR', $SO_2R$, COR and OR or a radical —CO—O—CO—, —CO—NR—CO—, which links two ortho positions, where R and R' each independently of one another are identical or different and are H, a straight-chain or branched alkyl having 1 to 6 carbon atoms, an aryl having 6 to 12 carbon atoms or aralkyl having 7 to 12 carbon atoms, and where the alkyls and aralkyls are unsubstituted or substituted from one to three times by halogen.

The abovementioned aromatic compounds may also contain additional substituents, examples being alkyl radicals or amino, alkylamino, hydroxyl or alkoxy groups.

It is possible to employ as starting material an aromatic compound which has on the ring system a fluorine-exchangeable chlorine or bromine substituent, especially a chlorine substituent, and which has as a further substituent at least one fluorine-exchangeable chlorine or bromine, especially chlorine, and which may have at least one further substituent from the series consisting of F, $NO_2$, $CF_3$, CN, CHO, COF, COCl, $SO_2F$, $SO_2Cl$, $OCF_3$, $SCF_3$, $SO_2CF_3$, COOR, CONRR', $SO_2R$, COR, OR, —CO—O—CO— and —CO—NR—CO—. Accordingly, these starting compounds possess at least two fluorine-exchangeable halogen substituents which independently of one another can be chlorine or bromine, especially chlorine. These compounds are usually amenable to single or double halogen-fluorine exchange without necessarily possessing a further substituent from the abovementioned series. They may, however, also possess a further substituent from the series of the abovementioned radicals which promotes the nucleophilic substitution of the aromatic compound. The presence of the substituents increases the reactivity of the aromatic compound in respect of the halogen-fluorine exchange reaction.

In the novel process it is possible with great success to employ a compound of the formula (III)

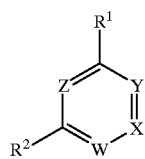

(III)

in which W is N or $C—R^3$, X is N or $C—R^4$, Y is N or $C—R^5$, Z is N or $C—R^6$ but, W, X and Y are not simultaneously N, $R^1$, $R^2$, $R^3$, $R^4$, $R^5$ and $R^6$ are identical or different and are H, F, Cl, Br, I, $NO_2$, NO, $CF_3$, CN, CHO, COF, COCl, $SO_2F$, $SO_2Cl$, $OCF_3$, $SCF_3$, $SO_2CF_3$, COOR, CONRR', $SO_2R$, COR, OR, or a radical —CO—O—CO—, —CO—NR—CO— or —CR"=CR"—CR"=CR"—, which links two ortho positions, R and R' are as defined above and radicals R" independently of one another are identical or different and have the same meaning as $R^1$ to $R^6$, and at least one of the radicals $R^1$ to $R^6$ is chlorine or bromine, especially chlorine.

A compound of the formula (III) can be employed in which $R^1$, $R^2$, $R^3$, $R^4$, $R^5$ and $R^6$ are identical or different and in particular are H, F, Cl, Br, $NO_2$, $CF_3$, CN, CHO, or COCl, preferably H, F, Cl, $NO_2$, CN or CHO.

It is also possible to employ a compound of the formula (III) in which only one of the radicals $R^1$ to $R^6$ is chlorine or bromine, especially chlorine, none of the radicals W, X, Y and Z is a nitrogen atom and at least one of the remaining radicals from the group $R^1$ to $R^6$ is $NO_2$, $CF_3$, CN, CHO, COF, COCl, $SO_2F$, $SO_2Cl$, $OCF_3$, $SCF_3$, $SO_2CF_3$, COOR, CONRR', $SO_2R$, COR, OR, —CO—O—CO—, —CO—NR—CO— or —CR"=CR"—CR"=CR"—.

In the process it is possible to employ a compound of the formula (III) in which 2 or more of the radicals $R^1$ to $R^6$ are chlorine or bromine, especially chlorine, the radicals W, X, Y and Z are 0 to 3 nitrogen atoms and the remaining radicals from the group $R^1$ to $R^6$ can all be hydrogen.

In the process it is also possible to employ a compound of the formula (III) in which only one of the radicals $R^1$ to $R^6$ is chlorine or bromine, especially chlorine, at least one of the radicals W, X, Y and Z is a nitrogen atom and the remaining radicals from the group $R^1$ to $R^6$ can all be hydrogen.

The incorporation of at least one nitrogen atom in the aromatic ring increases the reactivity of the aromatic compound such that a halogen-fluorine exchange is able to take place possibly even without the presence of a further substituent which promotes the nucleophilic substitution of the aromatic compound.

It is possible with great success to employ a compound of the formula (IV)

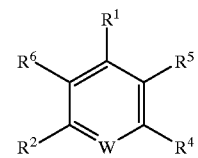

(IV)

in which W is N or $C—R^3$, one of the radicals $R^1$, $R^2$, $R^4$, $R^5$, $R^6$ and, if present, $R^3$, is Cl, F, $NO_2$, $CF_3$, CN, CHO, COF, COCl, $SO_2F$, $SO_2Cl$, $OCF_3$, $SCF_3$, $SO_2CF_3$, COOR, CONRR', $SO_2R$, COR or OR or two of the radicals which are ortho to one another are —CO—O—CO— or —CO—NR—CO—, where R and R' each independently of one another are identical or different and are H, a straight-chain or branched alkyl having 1 to 6 carbon atoms, an aryl having 6 to 12 carbon atoms or aralkyl having 7 to 12 carbon atoms, another of the radicals $R^1$, $R^2$, $R^4$, $R^5$, $R^6$ and, if present, $R^3$ is Cl and the remaining radicals are H, F or Cl.

With good prospect of success it is also possible to employ a compound of the formula (IV)

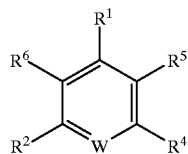
(IV)

in which W is N or C—R³, one of the radicals R¹, R², R⁴, R⁵, R⁶ or the radical R³ is Cl, F, NO₂, CF₃, CN, CHO, COF, COCl, SO₂F, SO₂Cl, OCF₃, SCF₃, SO₂CF₃, COOR, CONRR', SO₂R, COR or OR or two of the radicals which are ortho to one another are —CO—O—CO— or —CO—NR—CO—, where R and R' each independently of one another are identical or different and are H, a straight-chain or branched alkyl having 1 to 6 carbon atoms, an aryl having 6 to 12 carbon atoms or aralkyl having 7 to 12 carbon atoms, another of the radicals R¹, R², R⁴, R⁵ and R⁶ is Cl and the remaining radicals are H, F or Cl.

The radicals —CO—O—CO— and —CO—NR—CO— concern in general two of the radicals R¹ to R⁶ which are ortho to one another, especially two mutually ortho radicals from the group R¹, R², R⁴, R⁵ and R⁶, if W is N, or two mutually ortho radicals from the group R², R³ and R⁴, if W is C—R³.

In the compound of formula (IV) one of the radicals R¹, R², R⁴, R⁵, R⁶ and, if present, R³ or the radical R³ in particular is Cl, F, NO₂, CF₃, CN, CHO, COF, COCl, OCF₃, COOR, COONRR', COR, OR, —CO—O—CO— or —CO—NR—CO—, preferably Cl, F, NO₂, CF₃, CN, CHO, COOR or COCl, R and R' are in particular H, a straight-chain or branched alkyl having 1 to 4 carbon atoms or aryl having 6 to 12 carbon atoms, preferably H or a straight-chain or branched alkyl having 1 to 3 carbon atoms, particularly preferably methyl or ethyl, one or two of the radicals R¹, R², R⁴, R⁵, R⁶ and, if present, R³ is or are Cl, and the remaining radicals are identical or different and are H or Cl.

The formula (IV) given above embraces nonactivated compounds in which one of the radicals R¹, R², R⁴, R⁵, R⁶ and, if present, R³ is Cl or F and in addition one, two or more of the radicals R¹, R², R⁴, R⁵, R⁶ and, if present, R³ are Cl and the compounds resulting therefrom contain one, two or more Cl if one of the abovementioned radicals is F, or contain two, three or more Cl if one of the abovementioned radicals is not F but instead is Cl.

Examples of nonactivated pyridine derivatives of this kind in which W in formula (IV) is N are 2,3-dichloropyridine, 2,4-dichloropyridine, 2,5-dichloropyridine, 2,6-dichloropyridine, 3,4-dichloropyridine, 3,5-dichloropyridine, 2,3,4-trichloropyridine, 2,3,5-trichloropyridine, 2,3,6-trichloropyridine, 2,4,6-trichloropyridine, tetrachloropyridine and pentachloropyridine and also fluorinated chloropyridines formed from the abovementioned chloropyridines by partial fluorination.

Examples of nonactivated benzene derivatives of this kind in which W in formula (IV) is C—R³ are 1,2-dichlorobenzene, 1,3-dichlorobenzene, 1,4-dichlorobenzene, 1,2,3-trichlorobenzene, 1,2,4-trichlorobenzene, 1,3,5-trichlorobenzene, 1,2,3,4-tetrachlorobenzene, 1,2,3,5-tetrachlorobenzene, 1,2,4,5-tetrachlorobenzene, and also fluorinated chlorobenzenes which are formed from the abovementioned chlorobenzenes by partial fluorination.

The formula (IV) given above also embraces compounds which comprise an activating radical. A suitable activating radical is NO₂, CF₃, CN, CHO, COF, COCl, SO₂F, SO₂Cl, OCF₃, SCF₃, SO₂CF₃, COOR, COONRR', SO₂R, COR, OR, —CO—O—CO— or —CO—NR—CO—, especially NO₂, CF₃, CN, CHO, COF, COCl, OCF₃, COOR, CONRR', COR, OR, —CO—O—CO— or —CO—NR—CO—, preferably NO₂, CF₃, CN, CHO, COCl, COOR, COR.

In the case of the compounds which contain an activating radical one of the radicals R¹ to R⁶ in formula (IV), especially one of the radicals from the group R¹, R², R⁴, R⁵, and R⁶, if W is N, or especially the radical R³ if W is C—R³, is the activated radical. The activating radical is particularly effective if the Cl which is to be exchanged for F is ortho or para to the activating radical. In this context it should again be mentioned that the N atom in the pyridine ring is likewise activating in the context of a chlorine-fluorine exchange.

The novel process relates not only to the exchange of Cl ortho and/or para to an activating radical but also to the exchange of Cl in the less favored meta positions. Thus it is also possible to employ compounds of the formula (V)

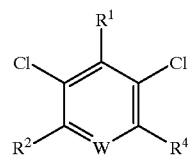
(V)

in which W is N or C—R³, where R³ is NO₂, CF₃, CN, CHO, COF, COCl, SO₂F, SO₂Cl, OCF₃, SCF₃, SO₂CF₃, COOR, COONRR', SO₂R, COR, or OR or are two radicals, in ortho position, from the group R², R³, R⁴ —CO—O—CO— and —CO—NR—CO—, in particular is NO₂, CF₃, CN, CHO, COF, COCl, OCF₃, COOR, CONRR', COR or OR or are two radicals, in ortho position, from the group R², R³ and R⁴, preferably NO₂, CF₃, CN, CHO or COCl, and R¹, R² and R⁴ are H, F or Cl.

The formulae (III), (IV) and (V), which are set out alongside one another below,

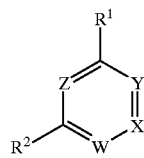
(III)

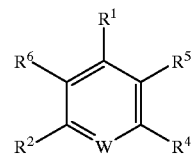
(IV)

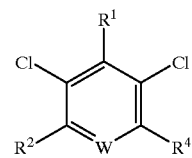
(V)

are interrelated in a clear way. If X in formula (III) is replaced by C—R⁴, Y by C—R⁵ and Z by C—R⁶, then the result is formula (IV). If R⁵ and R⁶ in formula (IV) are replaced by Cl, then formula (V) is obtained. Thus the formula (V) can also be derived from formula (III). Attention is drawn to this interrelationship at this point in order to avoid a possible misunderstanding.

With no claim to completeness the following substances which contain fluorine-exchangeable halogen are given as a small selection: 2-chloronitrobenzene, 2,4-dichloronitrobenzene, 2-chlorobenzaldehyde, 4chlorobenzaldehyde, 2-chlorobenzonitrile, 4-chlorobenzonitrile, 2-chlorobenzoyl chloride, 4-chlorobenzoyl chloride, 2,4-dichlorobenzaldehyde, 2,6-dichlorobenzaldehyde, 2,4-dichlorobenzonitrile, 2,6-dichlorobenzonitrile, 2,4-dichlorobenzoyl chloride and 2,6-dichlorobenzoyl chloride.

The fluoride of the formula (I) employed is calcium, ammonium, lithium, sodium, potassium, rubidium or cesium fluoride or a mixture thereof, especially lithium, sodium, potassium, rubidium or cesium fluoride or a mixture thereof, preferably sodium, potassium or cesium fluoride or a mixture thereof, and with particular preference potassium or cesium fluoride or a mixture thereof. It is in many cases sufficient to employ potassium fluoride alone.

As far as the proportion of fluoride to starting compounds is concerned, it should be borne in mind that there may be instances in which an excess of fluoride can lead to unwanted side reactions. In such cases it is advisable to employ a substoichiometric amount of fluoride as well. The ratio of fluoride of the formula (II) to equivalent of halogen to be exchanged is usually (0.5 to 10):1, in particular (0.8 to 5):1, preferably (1 to 2):1, and, with particular preference, (1 to 1.5):1.

As already mentioned at the outset, the reaction is conducted in the presence of a compound of the formula (II), which functions as catalyst.

The compounds of the formula (II) can be prepared, for example, by reacting phosphorus pentachloride with dialkylamines. The equation below shows the reaction using dimethylamine:

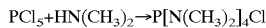

$$PCl_5 + HN(CH_3)_2 \rightarrow P[N(CH_3)_2]_4Cl$$

Alternatively, it is possible to react phosphorus pentachloride in stages with different secondary amines, for example dialkylamines, so as to obtain asymmetrically substituted compounds of the formula (II). Further options for synthesizing compounds of the formula (II) are described by R. Schwesinger et al. in Angew. Chem. 103 (1991) 1376 and in Chem. Ber. 127 (1994) 2435 to 2454.

It is possible to employ a compound of the formula (II) in which $A^1$, $A^2$, $A^3$, $A^4$, $A^5$, $A^6$, $A^7$ and $A^8$ independently of one another are identical or different and are straight-chain or branched alkyl or alkenyl, especially alkyl, having 1 to 12, especially 1 to 8, preferably 1 to 4 carbon atoms, or cycloalkyl having 4 to 8, especially 5 to 6 carbon atoms. These compounds are of particular interest because they can be prepared in a comparatively simple manner starting from the corresponding dialkylamines, dialkenylamines, dicycloalkylamines or secondary amines which comprise an alkyl and alkenyl radical, an alkyl and cycloalkyl radical or an alkenyl and cycloalkyl radical.

Examples of alkyl are methyl, ethyl, n-propyl, i-propyl, n-butyl, i-butyl, n-pentyl, 3-methylbutyl, n-hexyl and 2-ethylhexyl, especially methyl, ethyl, n-propyl and n-butyl, and examples of alkenyl are allyl, 2-propenyl and 2-n-butenyl, and examples of cycloalkyl are cyclopentyl, cyclohexyl, 4-methylcyclohexyl and 4-tert-butylcyclohexyl.

It is also possible to employ a compound of the formula (II) in which $A^1A^2$ $A^3A^4$ or $A^1A^2=A^3A^4=A^5A^6$ or $A^1A^2=A^3A^4=A^5A^6=A^7A^8$. These compounds, in which two or more of the groups $A^1A^2$, $A^3A^4$, $A^5A^6$ and $A^7A^8$ are identical to one another, are relatively easy to obtain.

It is also possible to employ a compound of the formula (II) in which $A^1=A^2$, $A^3=A^4$, $A^5=A^6$ and/or $A^7=A^8$. These compounds are comparatively easy to obtain and are therefore of interest.

It is also possible to employ a compound of the formula (II), in which $A^1=A^2=A^3=A^4$ or $A^1=A^2=A^3=A^4=A^5=A^6$ or $A^1=A^2=A^3=A^4=A^5=A^6=A^7=A^8$. These abovementioned compounds in which four, six or eight of the radicals $A^1$ to $A^8$ are identical are likewise of interest on the basis of their ready availability.

It is also possible to employ a compound of formula (II) in which $A^1A^2$ or $A^1A^2$ and $A^3$ $A^4$ or $A^1A^2$ and $A^3A^4$ and $A^5A^6$ or $A^1A^2$ and $A^3A^4$ and $A^5A^6$ and $A^7A^8$ are connected to one another directly or by way of O or N—$A^9$ to form a saturated or unsaturated ring having 5 or 6 ring members. Accordingly, these compounds comprise one, two, three or four of the abovementioned rings.

It is possible, furthermore, to employ a compound of the formula (II) in which $A^1A^2$ or $A^1A^2$ and $A^3$ $A^4$ or $A^1A^2$ and $A^3A^4$ and $A^5A^6$ or $A^1A^2$ and $A^3A^4$ and $A^5A^6$ and $A^7A^8$ are connected to form a ring whose ring members comprise the N atom on which the respective radicals $A^1$ to $A^8$ are located, if appropriate O or N—$A^9$, and $CH_2$-groups. In this group of substances the N atom together with the radicals $A^1$ to $A^8$ present thereon forms, for example, a hexahydropyridine ring, a tetrahydropyrrole ring, a hexahydropyrazine ring or a morpholine ring. Accordingly, these compounds comprise one, two, three or four of the abovementioned rings.

In the compound of the formula (II) $B^-$ is, as already mentioned above, a monovalent acid radical or the equivalent of a polyvalent acid radical, in particular the radical of an inorganic mineral acid, an organic carboxylic acid or an aliphatic or aromatic sulfonic acid.

It is usual to employ a compound of formula (II) in which $B^-$ is $F^-$, $Cl^-$, $Br^-$, $I^-$, $HF_2^-$, $BF_4^-$, $C_6H_5SO_3^-$, p-$CH_3$—$C_6H_5SO_3^-$, $HSO_4^-$, $PF_6^-$ or $CF_3SO_3^-$, especially $F^-$, $Cl^-$, $Br^-$, $I^-$, $HF_2^-$ or $BF_4^-$.

The compound of the formula (II) is employed in an amount of from 0.5 to 35, in particular from 1 to 30, and, preferably, from 3 to 25% by weight, based on the compound which contains fluorine-exchangeable halogen.

In order not to be governed exclusively by the abovementioned percentages by weight it is possible in a large number of cases to employ the compound of formula (II) in an amount of from 0.1 to 3, in particular from 0.4 to 5 and, preferably, from 0.5 to 1 mol-%, based on the compound which contains fluorine-exchangeable halogen. These amounts usually prove sufficient.

With no claim to completeness, the following may be mentioned as examples of compounds of the formula (II).
Tetrakis(dimethylamino)phosphonium chloride
Tetrakis(diethylamino)phosphonium chloride
Tetrakis(dimethylamino)phosphonium bromide
Tetrakis(diethylamino)phosphonium bromide
Tetrakis(dipropylamino)phosphonium chloride or bromide
Tris(diethylamino)(dimethylamino)phosphonium chloride or bromide
Tetrakis(dibutylamino)phosphonium chloride or bromide
Tris(dimethylamino)(diethylamino)phosphonium chloride or bromide
Tris(dimethylamino)(cyclopentylamino)phosphonium chloride or bromide
Tris(dimethylamino)(dipropylamino)phosphonium chloride or bromide
Tris(dimethylamino)(dibutylamino)phosphonium chloride or bromide Tris(dimethylamino)(cyclohexylamino)phosphonium chloride or bromide
Tris(dimethylamino)(diallylamino)phosphonium chloride or bromide
Tris(dimethylamino)(dihexylamino)phosphoniumchloride or bromide
Tris(diethylamino)(dihexylamino)phosphonium chloride or bromide
Tris(dimethylamino)(diheptylamino)phosphonium chloride or bromide
Tris(diethylamino)(diheptylamino)phosphonium chloride or bromide
Tetrakis(pyrrolidino)phosphonium chloride or bromide
Tetrakis(piperidino)phosphonium chloride or bromide
Tetrakis(morpholino)phosphonium chloride or bromide
Tris(piperidino)(diallylamino)phosphonium chloride or bromide
Tris(pyrrolidino)(ethylmethylamino)phosphonium chloride or bromide
Tris(pyrrolidino)(diethylamino)phosphonium chloride or bromide.

As catalyst it is possible to use a compound of the formula (II) or a mixture of two or more compounds of the formula (II). This is particularly simple if mixtures of compounds of the formula (II) as obtained in the synthesis are used.

As mentioned beforehand above the process can be conducted in the presence or absence of a solvent. If used, suitable solvents include not only dipolar-aprotic and aprotic but also protic solvents. Examples of suitable dipolar-aprotic solvents are dimethyl sulfoxide (DMSO), dimethyl sulfone, sulfolane (TMS), dimethylformamide (DMFA), dimethylacetamide, 1,3-dimethylimidazolin-2-one, N-methylpyrrolidone, hexamethylphosphoramide, acetonitrile and benzonitrile. These solvents can also be employed as a mixture.

Suitable aprotic solvents without a pronounced dipolar character are aromatic hydrocarbons or chlorinated aromatic hydrocarbons, for example benzene, toluene, ortho-, meta-, para-xylene, industrial mixtures of isomeric xylenes, ethylbenzene, mesitylene, ortho-, meta-, para-chlorotoluene, chlorobenzene and ortho-, meta-, para-dichlorobenzene. It is also possible to use mixtures of these solvents.

The aprotic or dipolar-aprotic solvents can be used in any desired amounts, for example from 5 to 500% by weight, although it is preferred to use small amounts in the region of from 5 to 30% by weight, based on the compound which contains fluorine-exchangeable halogen. If protic solvents are used the amounts employed are in the region of from 0.1 to 5, preferably from 0.1 to 2% by weight, based on the compound which contains fluorine-exchangeable halogen.

The reaction temperature depends also on the nature of the compound which contains fluorine-exchangeable halogen. Thus compounds which are comparatively slow to react in general require higher reaction temperatures, while comparatively reactive starting materials can be reacted successfully even at relatively low temperatures.

The same applies to the reaction times. Starting materials which are slow to react generally require longer reaction times than more reactive starting materials.

At this point attention should be drawn to the fact that exchange of only one halogen for fluorine is in general easier to carry out than exchange of two or more halogens for fluorine. Double or multiple halogen-fluorine exchange requires, if indeed it takes place at all, reaction conditions which are usually much more drastic (higher reaction temperatures and longer reaction times) than single halogen-fluorine exchange.

In a large number of cases it is sufficient to conduct the novel process at a temperature from 60 to 250° C., in particular from 90 to 220° C. and, preferably, from 120 to 200° C.

The novel process can be practiced either under reduced pressure or else under atmospheric or superatmospheric pressure. This possibility is utilized, for example, by supplying small amounts of a low-boiling aprotic solvent which forms an azeotrope with water, for example benzene, xylene, mesitylene, cyclohexane or toluene, to the reaction suspension before the beginning of the reaction. Subsequently, part of the solvent is removed again from the reaction suspension together with water by applying reduced pressure. This procedure makes it possible to increase the reaction rate and the yield and, in addition, to minimize the formation of byproducts.

The compound of the formula (II) can be used in the presence or absence of atmospheric oxygen. It is preferred to operate under inert gas, for example argon or nitrogen.

When conducting the process it should be ensured that the reaction mixture is thoroughly mixed during the entire reaction.

The process can be conducted discontinuously or continuously.

The examples which follow demonstrate the invention without restricting it.

EXPERIMENTAL SECTION

Preparation of 4-nitrofluorobenzene

Examples 1 and 2

Preparing 4-nitrofluorobenzene by Reacting 4-nitrochlorobenzene Using tetrakis(dimethylamino) phosphonium chloride as Catalyst A 1.5 l four-necked flask which is equipped with thermometer, anchor stirrer and reflux condenser with bubble counter is charged with 157 g (1 mol) of 4-nitrochlorobenzene, 400 ml of tetramethyl sulfone (TMS), (Example 1) or, respectively, 340 ml of dimethyl sulfoxide (DMSO) (Example 2), 62.7 g (1.1 mol) of potassium fluoride and 2.42 g (0.01 mol) of tetrakis(dimethylamino) phosphonium chloride. The mixture is then heated with stirring to the predetermined reaction temperature and is allowed to react for the predetermined time. After the end of the reaction the reaction mixture is cooled and dissolved in methylene chloride, insoluble constituents (salts such as KCl, KF) are removed by filtration, and the target product (4-nitrofluorobenzene) is purified by fractional distillation under reduced pressure.

Comparison Example 1

Preparing 4-nitrofluorobenzene by Reacting 4-nitrobenzene Using tetraphenylphosphonium bromide as Catalyst 157 g (1 mol) of 4-nitrochlorobenzene, 400 ml of tetramethylene sulfone, and 62.7 g (1.1 mol) of potassium fluoride, but 4.19 g (0.01 mol) of tetraphenylphosphonium bromide, are employed and the procedure described in Example 1 is followed.

Example 3

Preparing 4-nitrofluorobenzene by Reacting 4-nitrochlorobenzene Using tetrakis(diethylamino) phosphonium bromide as Catalyst A 500 ml four-necked flask which is equipped with thermometer, anchor stirrer and reflux condenser with bubble counter is charged with 157 g (1 mol) of 4-nitrochlorobenzene, 74.1 g (1.3 mol) of potassium fluoride and 3.99 g (0.01 mol) of tetrakis(diethylamino) phosphonium bromide but no solvent. The mixture is then heated with stirring to the predetermined reaction temperature and allowed to react for the predetermined time.

Subsequent workup is as indicated in Examples 1 and 2.

Comparison Example 2

Preparing 4-nitrofluorobenzene by Reacting 4-nitrochlorobenzene Using tetraphenylphosphonium bromide as Catalyst The procedure indicated in Example 3 is repeated but using, instead of the tetrakis(diethylamino)phosphonium bromide, 4.19 g (0.01 mol) of tetraphenylphosphonium bromide.

The reaction conditions (reaction temperature, time) and conversion and yield for Examples 1 to 3 and Comparison Examples 1 and 2 are given in Table 1 below.

157 g (1 mol) of 2-nitrochlorobenzene, 400 ml of dimethyl sulfoxide (DMSO), 68.4 g (1.2 mol) of potassium fluoride and 4.19 g (0.01 mol) of tetraphenylphosphonium bromide are employed and the procedure described in Example 4 is followed.

Comparison Example 4

Preparing 2-nitrofluorobenzene by Reacting 2-nitrochlorobenzene Using 18-crown-6-ether as Catalyst 157 g (1 mol) of 2-nitrochlorobenzene, 480 ml of dimethyl sulfoxide, 68.4 g (1.2 mol) of potassium fluoride and 2.64 g (0.01 mol) of 18-crown-6-ether are employed and the procedure described in Example 5 is followed.

Example 6

Preparing 2-nitrofluorobenzene by Reacting 2-nitrochlorobenzene Using tetrakis(diethylamino) phosphonium bromide as Catalyst A 500 ml four-necked flask which is equipped with thermometer, anchor stirrer and reflux condenser with

TABLE 1

Preparation of 4-nitrofluorobenzene

| | 4-Nitro-chlorobenzene | Solvent | KF | Catalyst | Time (hours) | Reaction temperature | Conversion % | Yield % |
|---|---|---|---|---|---|---|---|---|
| Ex. 1 | 1 mol | 400 ml TMS | 1.1 mol | 0.01 mol A | 5 | 180° C. | 100 | 85 |
| Comp. Ex. 1 | 1 mol | 400 ml TMS | 1.1 mol | 0.01 mol B | 5 | 180° C. | 71 | 52 |
| Ex. 2 | 1 mol | 340 ml DMSO | 1.1 mol | 0.01 mol A | 5 | 180° C. | 100 | 86 |
| Ex. 3 | 1 mol | — | 1.3 mol | 0.013 mol C | 10 | 190° C. | 99 | 76 |
| Comp. Ex. 2 | 1 mol | — | 1.3 mol | 0.013 mol B | 10 | 190° C. | 46 | 32 |

TMS = Tetramethylene sulfone (Sulfolane)
DMSO = Dimethyl sulfoxide
Catalyst:
A = Tetrakis(dimethylamino)phosphonium chloride [$(CH_3)_2N]_4PCl$
B = Tetraphenylphosphonium bromide $(C_6H_5)_4PBr$
C = Tetrakis(diethylamino)phosphonium bromide [$(C_2H_5)_2N]_4PBr$ Preparation of 2-nitrofluorobenzene Examples 4 and 5

Preparing 2-nitrofluorobenzene by Reacting 2-nitrochlorobenzene Using tetrakis(diethylamino) phosphonium bromide as Catalyst A 1.5 l four-necked flask which is equipped with thermometer, anchor stirrer and reflux condenser with bubble counter is charged with 157 g (1 mol) of 2-nitrochlorobenzene, 400 ml of dimethyl sulfoxide (DMSO) (Example 4) or, respectively, 480 ml of tetramethylene sulfone (TMS) (Example 5), 68.4 g (1.2 mol) of potassium fluoride and 3.99 g (0.01 mol) of tetrakis (diethylamino)phosphonium bromide. The reaction mixture is then heated with stirring to the predetermined reaction temperature and is allowed to react for the time indicated.

Subsequent workup is as described in Examples 1 and 2.

Comparison Example 3

Preparing 2-nitrofluorobenzene by Reacting 2-nitrochlorobenzene Using tetraphenylphosphonium bromide as Catalyst bubble counter is charged with 157 g (1 mol) of 2-nitrochlorobenzene, 68.4 g (1.2 mol) of potassium fluoride and 3.99 g (0.01 mol) of tetrakis(diethylamino) phosphonium bromide but no solvent. The reaction mixture is then heated with stirring to the predetermined reaction temperature and is allowed to react for the time indicated.

Subsequent workup is as described in Examples 1 and 2.

Comparison Example 5

Preparing 2-nitrofluorobenzene by Reacting 2-nitrochlorobenzene Using tetraphenylphosphonium bromide as Catalyst The procedure indicated in Example 6 is repeated but using, instead of tetrakis(diethylamino)phosphonium bromide, 4.19 g (0.01 mol) of tetraphenylphosphonium bromide.

The reaction conditions (reaction temperature, time) and conversion and yield for Examples 4 to 6 and Comparison Examples 4 and 5 are given in Table 2 below.

TABLE 2

Preparation of 2-nitrofluorobenzene

|  | 2-Nitro-chlorobenzene | Solvent | KF | Catalyst | Time (Hours) | Reaction temperature | Conversion % | Yield % |
|---|---|---|---|---|---|---|---|---|
| Ex. 4 | 1 mol | 400 ml DMSO | 1.2 mol | 0.01 mol C | 5 | 180° C. | 98 | 74 |
| Comp. Ex. 3 | 1 mol | 400 ml DMSO | 1.2 mol | 0.01 mol B | 5 | 180° C. | 42 | 31 |
| Ex. 5 | 1 mol | 480 ml TMS | 1.2 mol | 0.01 mol C | 7 | 180° C. | 100 | 85 |
| Comp. Ex. 4 | 1 mol | 480 ml TMS | 1.2 mol | 0.01 mol D | 7 | 180° C. | 33 | 20 |
| Ex. 6 | 1 mol | — | 1.2 mol | 0.01 mol C | 10 | 190° C. | 99 | 71 |
| Comp. Ex. 5 | 1 mol | — | 1.2 mol | 0.01 mol B | 10 | 190° C. | 42 | 30 |

DMSO = Dimethyl sulfoxide
TMS = Tetramethylene sulfone (Sulfolane)
Catalyst:
C = Tetrakis(diethylamino)phosphonium bromide [$(C_2H_5)_2N]_4PBr$
B = Tetraphenylphosphonium bromide $(C_6H_5)_4PBr$
D = 18-crown-6 ether Preparation of 2,4-difluoronitrobenzene Examples 7 and 8

Preparing 2,4-difluoronitrobenzene by Reacting 2,4-dichloronitrobenzene

A 1.5 l four-necked flask which is equipped with thermometer, anchor stirrer and reflux condenser with bubble counter is charged with 192 g (1 mol) of 2,4-dichloronitrobenzene, 550 ml of tetramethylene sulfone (TMS), 136.8 g (2.4 mol) of potassium fluoride and 5.99 g (0.015 mol) of tetrakis(diethylamino)phosphonium bromide (Example 7) or, respectively, 3.63 g (0.015 mol) of tetrakis(dimethylamino)phosphonium chloride (Example 8).

The reaction mixture is then heated with stirring to the predetermined reaction temperature and allowed to react for the time indicated.

Subsequent workup is as described in Examples 1 and 2.

Comparison Example 6

Preparing 2,4-difluoronitrobenzene by Reacting 2,4-dichloronitrobenzene Using tetraphenylphosphonium bromide as Catalyst 192 g (1 mol) of 2,4-dichloronitrobenzene, 550 ml of tetramethylene sulfone, 136.8 g (2.4 mol) of potassium fluoride and 6.29 g (0.015 mol) of tetraphenylphosphonium bromide are employed and the procedure described in Example 7 and 8 is followed.

Examples 9 and 10

Preparing 2,4-difluoronitrobenzene by Reacting 2,4-dichloronitrobenzene

A 500 ml four-necked flask which is equipped with thermometer, anchor stirrer and reflux condenser with bubble counter is charged with 192 g (1 mol) of 2,4-dichloronitrobenzene, 136.8 g (2.4 mol) of potassium fluoride, 7.98 g (0.02 mol) of tetrakis(diethylamino)phosphonium bromide (Example 9) or, respectively, 8.54 g (0.02 mol) of ethylbutylaminotris(diethylamino)phosphonium bromide (Example 10) but no solvent. The reaction mixture is then heated with stirring to the predetermined reaction temperature and allowed to react for the time indicated.

Subsequent workup is as described in Examples 1 and 2.

Comparison Example 7

Preparing 2,4-difluoronitrobenzene by Reacting 2,4-dichloronitrobenzene Using tetraphenylphosphonium bromide as Catalyst (No Solvent)

The procedure described in Examples 8 and 9 is repeated but using, instead of tetrakis(diethylamino)phosphonium bromide or, respectively, ethylbutylaminotris(diethylamino) phosphonium bromide, 8.38 g (0.02 mol) of tetraphenylphosphonium bromide.

The reaction conditions (reaction temperature, time) and conversion and yield for Examples 7 to 10 and Comparison Examples 6 and 7 are given in Table 3 below.

TABLE 3

Preparation of 2,4-difluoronitrobenzene

|  | 2,4-Dichloro-nitro-benzene | Solvent | KF | Catalyst | Time (Hours) | Reaction temperature | Conversion % | Yield % |
|---|---|---|---|---|---|---|---|---|
| Ex. 7 | 1 mol | 500 ml TMS | 2,4 mol | 0.015 mol C | 6 | 180° C. | 99 | 75 |
| Ex. 8 | 1 mol | 550 ml TMS | 2,4 mol | 0.015 mol A | 6 | 180° C. | 97 | 78 |
| Comp. Ex. 6 | 1 mol | 550 ml TMS | 2,4 mol | 0.015 mol B | 6 | 180° C. | 73 | 51 |
| Ex. 9 | 1 mol | — | 2,4 mol | 0.02 mol C | 10 | 190° C. | 100 | 69 |
| Ex. 10 | 1 mol | — | 2,4 mol | 0.02 mol E | 10 | 190° C. | 100 | 75 |
| Comp. Ex. 7 | 1 mol | — | 2,4 mol | 0.02 mol B | 10 | 190° C. | 48 | 35 |

TMS = Tetramethylene sulfone (sulfolane)
Catalyst:
A = Tetrakis(dimethylamino)phosphonium chloride [$(CH_3)_2N]_4PCl$
B = Tetraphenylphosphonium bromide $(C_6H_5)_4PBr$
C = Tetrakis(diethylamino)phosphonium bromide [$(C_2H_5)_2N]_4PBr$
E = Ethylbutylaminotris(diethylamino)phosphonium bromide

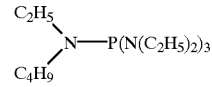

Preparation of 2,3-difluoro-5-chloropyridine

Example 11

Preparing 2,3-difluoro-5-chloropyridine by Reacting 2-fluoro-3,5-dichloropyridine Using tetrakis(diethylamino)phosphonium bromide A 500 ml four-necked flask which is equipped with thermometer, anchor stirrer and reflux condenser with bubble counter is charged with 166 g (1 mol) of 2-fluoro-3,5-dichloropyridine, 68.4 g (1.2 mol) of potassium fluoride and 3.99 g (0.01 mol) of tetrakis(diethylamino)phosphonium bromide. The reaction mixture is then heated with stirring to the predetermined reaction temperature and is allowed to react for the time indicated.

After the end of the reaction the reaction mixture is cooled and poured into water which is employed in excess, the mixture is subjected to extraction with methylene chloride, and the isolated methylene chloride phase is washed with water, dried and then subjected to fractional distillation under reduced pressure.

Comparison Example 8

Preparing 2,3-difluoro-5-chloropyridine by Reacting 2-fluoro-3,5-dichloropyridine Using tetraphenylphosphonium bromide as Catalyst 166 g (1 mol) of 2-fluoro-3,5-dichloropyridine, 68.4 g (1.2 mol) of potassium fluoride and 4.19 g (0.01 mol) of tetraphenylphosphonium bromide are employed and the procedure described in Example 11 is followed.

The reaction conditions (reaction temperature, time) and conversion and yield for Example 11 and Comparison Example 8 are given in Table 4 below.

Preparation of 1-fluoro-3,5-dichlorobenzene and 1,3-difluoro-5-chlorobenzene

Example 12

Preparing 1-fluoro-3,5-dichlorobenzene and 1,3-difluoro-5-chlorobenzene by Reacting 1,3,5-trichlorobenzene Using tetrakis(diethylamino)phosphonium bromide A 500 ml four-necked flask which is equipped with thermometer, anchor stirrer and reflux condenser with bubble counter is charged with 181.5 g (1 mol) of 1,3,5-trichlorobenzene, 136.8 g (2.4 mol) of potassium fluoride and 7.98 g (0.02 mol) of tetrakis(diethylamino)phosphonium bromide. The reaction mixture is then heated with stirring to a predetermined reaction temperature and allowed to react for the time indicated. After the end of the reaction the reaction mixture is cooled and dissolved in methylene chloride, insoluble constituents (salts such as KCl, KF) are removed by filtration, and the target products (1-fluoro-3,5-dichlorobenzene and 1,3-difluoro-5-chlorobenzene) are purified by fractional distillation.

The reaction conditions (reaction temperature, time) and conversion and yield for Example 12 are given in Table 4 below.

Preparation of 1,2,3,4-tetrafluorobenzotrifluoride

Example 13

Preparing 1,2,3,4-tetrafluorobenzotrifluoride by Reacting 1,2,3,4-tetrachlorobenzotrifluoride Using tetrakis(diethylamino)phosphonium bromide as Catalyst A 1000 ml four-necked flask which is equipped with thermometer, anchor stirrer and reflux condenser with bubble counter is charged with 284 g (1 mol) of 1,2,3,4- tetrachlorobenzotrifluoride, 285 g (5 mol) of potassium fluoride and 15.96 g (0.04 mol) of tetrakis(diethylamino) phosphonium bromide. The reaction mixture is then heated with stirring to the predetermined reaction temperature and allowed to react for the time indicated.

After the end of the reaction the reaction mixture is cooled and dissolved in methylene chloride, insoluble constituents (salts such as KCl, KF) are removed by filtration, and the target product (1,2,3,4-tetrafluorobenzotrifluoride) is purified by fractional distillation.

Comparison Example 9

Preparing 1,2,3,4-tetrafluorobenzotrifluoride by Reacting 1,2,3,4-tetrachlorobenzotrifluoride Using tetraphenylphosphonium bromide as Catalyst 284 g (1 mol) of 1,2,3,4-tetrachlorobenzotrifluoride, 285 g (5 mol) of potassium fluoride and 16.76 g (0.04 mol) of tetraphenylphosphonium bromide are employed and the procedure described in Example 13 is followed.

The reaction conditions (reaction temperature, time) and conversion and yield for Example 13 and Comparison Example 9 are given in Table 4 below.

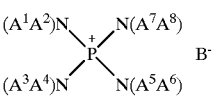

(II)

in which $A^1, A^2, A^3, A^4, A^5, A^6, A^7, A^8$ independently of one another are identical or different and are a straight-chain or branched alkyl or alkenyl having 1 to 12 carbon atoms, cycloalkyl having 4 to 8 carbon atoms, an aryl having 6 to 12 carbon atoms, or an aralkyl having 7 to 12 carbon atoms, or $A^1$ $A^2$, $A^3A^4$, $A^5A^6$, and $A^7A^8$ independently of one another are identical or different and are connected to one another directly or by way of O or N—$A^9$ to form a ring having 3 to 7 ring members, $A^9$ is an alkyl having 1 to 4 carbon atoms and $B^-$ is a monovalent acid radical or the equivalent of a polyvalent acid radical.

2. The process as claimed in claim 1, wherein the compound employed which contains fluorine-exchangeable halogen is an aromatic compound whose ring system has from 0 to 3 nitrogen atoms and carries a chlorine or bromine substituent which can be exchanged for fluorine, which

TABLE 4

Preparation of 2,3-difluoro-5-chloropyridine, 1-fluoro-3,5-dichlorobenzene, 1,3-difluoro-5-chlorobenzene and 1,2,3,4-tetrafluorobenzotrifluoride without addition of a solvent

| | Starting material | KF | Catalyst | Time (Hours) | Reaction temperature | Conversion % | Yield % |
|---|---|---|---|---|---|---|---|
| Ex. 1 | 1 mol 2-fluoro-3,5-dichloro-pyridine | 1.2 mol | 0.01 mol C | 4 | 170° C. | 55 | 40 |
| Comp. Ex. 8 | 1 mol 2-fluoro-3,5-dichloro-pyridine | 1.2 mol | 0.01 mol B | 4 | 170° C. | 5 | 1–2 |
| Ex. 12 | 1 mol 1,3,5-tri-chlorobenzene | 2.4 mol | 0.02 mol C | 10 | 180° C. | 100 | 50* 37** |
| Ex. 13 | 1 mol 1,2,3,4-tetra-chlorobenzo-trifluoride | 5 mol | 0.04 mol C | 10 | 190° C. | 96 | 68 |
| Comp. Ex. 9 | 1 mol 1,2,3,4-tetra-chlorobenzo-trifluoride | 5 mol | 0.04 mol B | 10 | 190° C. | 35 | 20 |

*Yield of 1-fluoro-3,5-dichlorobenzene
**Yield of 1,3-difluoro-5-chlorobenzene
Catalyst:
B = Tetraphenylphosphonium bromide $(C_6H_5)_4PBr$
C = Tetrakis(diethylamino)phosphonium bromide $[(C_2H_5)_2N]_4PBr$

What is claimed is:

1. A process for preparing fluorine-containing compounds by reacting a compound which contains fluorine-exchangeable halogen with a fluoride or a mixture of fluorides with the formula I MeF (I), in which Me is an alkaline earth metal ion, $NH_4^+$-ion or alkali metal ion, in the presence or absence of a solvent at a temperature from 40 to 260° C., which comprises carrying out the reaction in the presence of a compound or a mixture of compounds of the formula (II)

compound may have at least one further substituent which promotes the nucleophilic substitution of the aromatic compounds.

3. The process as claimed in claim 1, wherein an aromatic compound is employed which has on the ring system a fluorine-exchangeable chlorine or bromine substituent and has at least one further substituent from the series consisting of F, Cl, Br, I, $NO_2$, $CF_3$, CN, CHO, COF, COCl, $SO_2F$, $SO_2Cl$, $OCF_3$, $SCF_3$, $SOCF_3$, $SO_2CF_3$, COOR, CONRR', $SO_2R$, COR, OR or a radical —CO—O—CO—, —CO—NR—CO—, which links two ortho positions, where R and R' each independently of one another are identical or different and are H, a straight-chain or branched alkyl having 1 to 6 carbon atoms, an aryl having 6 to 12 carbon atoms or aralkyl having 7 to 12 carbon atoms and where the alkyls and aralkyls are unsubstituted or substituted from one to three times by halogen.

4. The process as claimed in claim 1, wherein an aromatic compound is employed which has on the ring system a fluorine-exchangeable chlorine or bromine substituent and has at least one fluorine-exchangeable chlorine or bromine as further substituent and may have at least one further substituent from the series consisting of F, $NO_2$, $CF_3$, CN, CHO, COF, COCl, $SO_2F$, $SO_2Cl$, $OCF_3$, $SCF_3$, $SO_2CF_3$, COOR, CONRR', $SO_2R$, COR, OR, —CO—O—CO— and —CO—NR—CO—.

5. The process as claimed in claim 1, wherein a compound of the formula (III) is employed

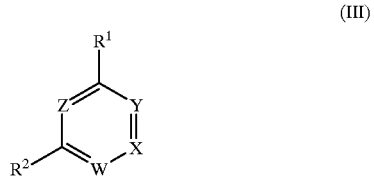

(III)

in which W is N or C—$R^3$, X is N or C—$R^4$, Y is N or C—$R^5$, Z is N or C—$R^6$ but, W, X and Y are not simultaneously N, $R^1$, $R^2$, $R^3$, $R^4$, $R^5$ and $R^6$ are identical or different and are H, F, Cl, Br, I, $NO_2$, $CF_3$, CN, CHO, COF, COCl, $SO_2F$, $SO_2Cl$, $OCF_3$, $SCF_3$, $SO_2CF_3$, COOR, CONRR', $SO_2R$, COR, OR, or a radical —CO—O—CO—, —CO—NR—CO— or —CR"=CR"—CR"=CR"—, which links two ortho positions, R and R' are as defined above and radicals R" independently of one another are identical or different and have the same meaning as $R^1$ to $R^6$, and at least one of the radicals $R^1$ to $R^6$ is chlorine or bromine.

6. A process as claimed in claim 1, wherein a compound of the formula (III) is employed in which only one of the radicals $R^1$ to $R^6$ is chlorine or bromine, none of the radicals W, X, Y and Z is a nitrogen atom and at least one of the remaining radicals from the group $R^1$ to $R^6$ is $NO_2$, $CF_3$, CN, CHO, COF, COCl, $SO_2F$, $SO_2Cl$, $OCF_3$, $SCF_3$, $SO_2CF_3$, COOR, COONRR', $SO_2R$, COR, OR, —CO—O—CO—, —CO—NR—CO— or —CR"=CR"—CR"=CR"—.

7. The process as claimed in claim 1, wherein a compound of the formula (III) is employed in which two or more of the radicals $R^1$ to $R^6$ are chlorine or bromine, radicals W, X, Y and Z are from 0 to 3 nitrogen atoms and the remaining radicals from the group $R^1$ to $R^6$ can all be hydrogen.

8. The process as claimed in claim 1, wherein the fluoride of the formula (I) employed is lithium, sodium, potassium, rubidium or cesium fluoride or a mixture thereof.

9. The process as claimed in claim 1, wherein the ratio of the fluoride of the formula (II) to equivalent of halogen to be exchanged is (0.5 to 10): (1).

10. The process as claimed in claim 1, wherein a compound of the formula (II) is employed in which $A^1$, $A^2$, $A^3$, $A^4$, $A^5$, $A^6$, $A^7$ and $A^8$ independently of one another are identical or different and are straight-chain or branched alkyl or alkenyl having 1 to 12 carbon atoms or cycloalkyl having 4 to 8 carbon atoms.

11. The process as claimed in claim 1 wherein a compound of the formula (II) is employed in which $A^1$, $A^2$, $A^3$, $A^4$, $A^5$, $A^6$, $A^7$ and $A^8$ independently of one another are identical or different and are straight-chain or branched alkyl or alkenyl having 1 to 8 carbon atoms or cycloalkyl having 5 to 6 carbon atoms.

12. The process as claimed in claim 1 wherein a compound of the formula (II) is employed in which $A^1$, $A^2$, $A^3$, $A^4$, $A^5$, $A^6$, $A^7$ and $A^8$ independently of one another are identical or different and are straight-chain or branched alkyl or alkenyl having 1 to 4 carbon atoms.

13. The process as claimed in claim 1, wherein a compound of the formula (II) is employed in which $A^1A^2=A^3A^4$ or $A^1A^2=A^3A^4=A^5A^6$ or $A^1A^2=A^3A^4=A^5A^6=A^7A^8$.

14. The process as claimed in claim 1, wherein a compound of the formula (II) is employed in which $A^1=A^2=A^3=A^4$ or $A^1=A^2=A^3=A^4=A^5=A^6$ or $A^1=A^2=A^3=A^4=A^5=A^6=A^7=A^8$.

15. The process as claimed in claim 1, wherein a compound of the formula (II) is employed in which $A^1A^2$ or $A^1A^2$ and $A^3A^4$ or $A^1A^2$ and $A^3A^4$ and $A^5A^6$ or $A^1A^2$ and $A^3A^4$ and $A^5A^6$ and $A^7A^8$ are joined to one another directly or by way of O or N—$A^9$ to form a saturated or unsaturated ring with 5 or 6 ring members.

16. The process as claimed in claim 1, wherein a compound of the formula (II) is employed in which $A^1A^2$ or $A^1A^2$ and $A^3A^4$ or $A^1A^2$ and $A^3A^4$ and $A^5A^6$ or $A^1A^2$ and $A^3A^4$ and $A^5A^6$ and $A^7A^8$ are joined to form a saturated or unsaturated ring whose ring members comprise the N atom on which the respective radicals $A^1$ to $A^8$ are located, if appropriate O or N—$A^9$, and $CH_2$ groups.

17. The process as claimed in claim 1, wherein a compound of the formula (II) is employed in which $B^-$ is $F^-$, $Cl^-$, $Br^-$, $HF_2^-$, $I^-$, $BF_4^-$, $C_6H_5SO_3^-$, p-$CH_3$—$C_6H_4$—$SO_3^-$, $HSO_4^-$, $PF_6^-$, or $CF_3SO_3^-$.

18. The process as claimed in claim 1, wherein a compound of the formula (II) is employed in which $B^-$ is $F^-$, $Cl^-$, $Br^-$, $HF_2^-$ or $BF_4^-$.

19. The process as claimed in claim 1, wherein the compound of the formula (II) is employed in an amount of from 0.5 to 35% by weight, based on the compound which contains fluorine-exchangeable halogen.

20. The process as claimed in claim 1, wherein the solvent employed is a dipolar-aprotic, an aprotic or a protic solvent.

21. The process as claimed in claim 1, wherein the dipolar-aprotic solvent employed is dimethyl sulfoxide, dimethyl sulfone, sulfolane, dimethylformamide, dimethylacetamide, 1,3-dimethylimidazolin-2-one, N-methylpyrrolidone, hexamethyiphosphoramide, acetonitrile or benzonitrile or a mixture of these solvents.

22. The process as claimed in claim 1, wherein the aprotic solvent employed is an aromatic hydrocarbon, a chlorinated aromatic hydrocarbon or a mixture of these solvents.

23. The process as claimed in claim 1, wherein the aprotic solvent employed is benzene, toluene, ortho-, meta-, para-xylene, industrial mixtures of isomeric xylenes, ethylbenzene, mesitylene, ortho-, meta-, para-chlorotoluene, chlorobenzene, ortho-, meta-, para-dichlorobenzene or a mixture of these solvents.

24. The process as claimed in claim 1, wherein the protic solvent employed is methanol, ethanol, propanol, isopropanol, butanol, isobutanol, polyalkylene glycols having ethylene, propylene or butylene units, or a mixture of these solvents.

25. The process as claimed in claim 1, wherein the reaction is conducted at from 60 to 250° C.

26. The process as claimed in claim 1, wherein the reaction is conducted at from 90 to 220° C.

27. The process as claimed in claim 1, wherein the reaction is conducted at from 120 to 200° C.

* * * * *